United States Patent [19]

Tsugita et al.

[11] Patent Number: 5,439,650

[45] Date of Patent: * Aug. 8, 1995

[54] REACTION VESSEL

[75] Inventors: Akira Tsugita, Kashowa; Masaharu Kamo, Noda; Toyoaki Uchida, Tokyo; Ikuo Nanno, Narashino; Yasuhiro Nomoto; Seitaro Takahashi, both of Tokyo, all of Japan

[73] Assignees: Seiko Instruments Inc.; Seiko Seiki Kabushiki Kaisha, Japan

[*] Notice: The portion of the term of this patent subsequent to Aug. 4, 2009 has been disclaimed.

[21] Appl. No.: 970,941

[22] Filed: Nov. 3, 1992

Related U.S. Application Data

[63] Continuation of Ser. No. 449,528, Dec. 11, 1989, abandoned.

[30] Foreign Application Priority Data

Dec. 9, 1988 [JP] Japan .................. 63-311317

[51] Int. Cl.⁶ .......................... B01S 8/20; G05F 7/00
[52] U.S. Cl. ..................... 422/108; 422/102; 422/104; 422/116; 422/129; 435/289; 436/526; 436/807
[58] Field of Search ............. 422/129, 130, 211, 212, 422/99, 102, 108, 116, 104; 435/289, 299, 173.1–173.9, 173; 436/526, 807

[56] References Cited

U.S. PATENT DOCUMENTS

| | | | |
|---|---|---|---|
| 3,635,678 | 1/1972 | Seitz et al. | 436/69 |
| 3,892,531 | 7/1975 | Gilbert | 422/116 |
| 3,981,776 | 9/1976 | Saxholm | 435/299 |
| 4,115,535 | 9/1978 | Giaever | 436/526 |
| 4,141,687 | 2/1979 | Forrest et al. | 436/526 |
| 4,454,234 | 6/1984 | Czerlinski | 436/526 |
| 4,578,169 | 3/1986 | Vicario et al. | 422/102 |
| 4,701,304 | 10/1987 | Horn et al. | 422/108 |
| 4,882,127 | 11/1989 | Rosenthal et al. | 422/116 |
| 4,913,883 | 4/1990 | Imai et al. | 436/526 |
| 4,990,075 | 2/1991 | Wogoman | 436/526 |
| 5,135,720 | 8/1992 | Uchida | 436/526 |

FOREIGN PATENT DOCUMENTS

| | | | |
|---|---|---|---|
| 0144437 | 6/1985 | European Pat. Off. | |
| 0240770 | 10/1987 | European Pat. Off. | |
| 0207058 | 10/1985 | Japan | 436/526 |
| 1232277 | 5/1986 | U.S.S.R. | 422/186.01 |

*Primary Examiner*—Peter Kratz
*Attorney, Agent, or Firm*—Adams & Wilks

[57] ABSTRACT

An reaction vessel utilizes a sample carrier composed of a magnetic core and a surface coating effective to support sample of protein or peptide. The sample carrier is floated magnetically and positioned within a reaction chamber. Edman reagent is applied to the sample to effect amino acid sequence analysis of protein or peptide from amino-terminal. By such construction, reaction efficiency is increased to produce sequentially thiazolinon amino-acid derivatives to thereby increase number of identified remaining amino acids, thereby enabling microanalysis of sample.

16 Claims, 4 Drawing Sheets

REACTION VESSEL

This is a continuation of parent application Ser. No. 449,528 filed Dec. 11, 1989, and now abandoned.

BACKGROUND OF THE INVENTION

The present invention relates to a reaction vessel for carrying out reactions which sequentially produce thiazolinon amino acid derivatives in an analyzer which automate amino-terminal sequence analysis of protein or peptide.

FIGS. 6 and 7 show two types of conventional reaction vessel for carrying out reactions which sequentially produce thiazolinon amino acid derivatives based on the Edman reaction.

The conventional reaction vessel of FIG. 6 is constructed such that a sample is adsorbed in a glass filter 31 on a membrane filter 30 sandwiched by a pair of glass blocks 29a and 29b within a frame 28, and a reagent or solvent is fed to the sample through a flow path in the center of the glass blocks.

The other conventional reaction vessel shown in FIG. 7 comprises a reaction chamber 34 connected to a vacuum pump 32 and to a nitrogen gas bottle 33 through a three-way switch valve 31 to create a vacuum in the reaction chamber or to fill the reaction chamber with nitrogen gas. The reaction chamber 34 is composed of a glass cup 36 which is rotatable by a motor 35, a supply line 37 for feeding reagent and solvent needed for reaction, into the glass cup 36 and a discharge line 38 for removing the reagent and solvent.

However, with regard to the FIG. 6 conventional reaction vessel, the sample is supported between glass fibers of the glass filter 30 and therefore the reagent or solvent cannot be efficiently distributed. Hence the reactions become nonuniform. Thereby repeatitive yield in the sequence analysis is reduced. Such tendency becomes remarkable in the case of a micro amount of sample to thereby make the analysis not possible. Further, various kinds of reagents and solvents are supplied through a common flow path to the protein sample for the reaction. Therefore, these substances may be contaminated by each other.

With regard to the FIG. 7 conventional reaction vessel, the structure for rotation of the sample is contained in the vacuum chamber. Therefore the maintenance of the analyzer is complicated. In particular, because the glass cup for treating a micro amount of the sample is small, it is difficult to maintain the stable rotation of such a small glass cup.

SUMMARY OF THE INVENTION

An object of the present invention is to, therefore, eliminate the above noted drawbacks of the prior art.

According to the present invention, the reaction vessel is comprised of a separatable reaction chamber made of nonmagnetic material, a sample carrier having spheric or elliptic body shape composed of magnetic material which is laminated with a film disposed in the reaction chamber, magnetic means disposed outside the reaction chamber for levitating and holding the sample carrier by magnetic force, a support structure for supporting the magnetic means, driving device for driving the support structure, a sensor for detecting a position of the sample carrier, and adjusting means for adjusting the position of the sample carrier.

In such a construction of the reaction vessel, a sample of protein or peptide is uniformly dispersed on the laminate film of the sample carrier in the sample chamber, and the sample carrier is floated and held so as to increase the reaction efficiency between the sample and the reagent or solvent. Furthermore, contamination of these reagents and solvents with each other can be decreased as much as possible.

BRIEF DESCRIPTION OF THE DRAWINGS

FIGS. 1–5 show embodiments of the reaction vessel according to the present invention, wherein FIG. 1 is a sectional view of the reaction vessel, FIG. 2 is a control block diagram of electromagnets 4 and position sensors 5, FIG. 3 is a sectional view of a sample carrier;

FIG. 4 shows a separation pattern of a standard mixture of phenylthiocarbamyl amino acid derivatives;

FIG. 5 is a partial perspective view of another reaction vessel; and

DETAILED DESCRIPTION OF PREFERRED EMBODIMENTS

Hereinafter, embodiments of the present invention will be described in conjunction with the drawings.

Figure 1:
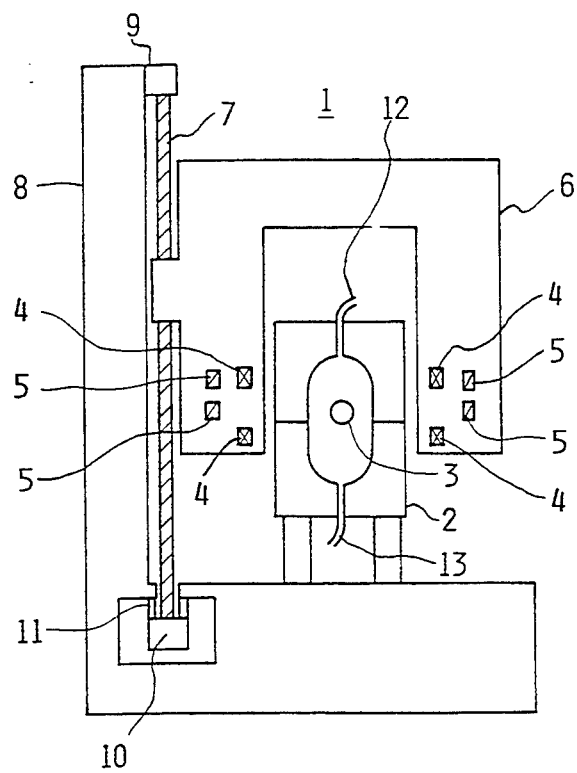

Firstly, one embodiment is described to show how to levitate and hold a sample carrier in a reaction chamber. In the reaction vessel or apparatus 1 shown in FIG. 1, a reaction chamber 2 is provided therein with a sample carrier 3 which carries a protein sample and is composed of magnetic material and is levitated inside the chamber. This levitating and holding is effected by magnetic levitation means including magnetic force generated by electromagnets 4, and the position of the sample carrier 3 is monitored by sensing means including position sensors 5 which generate detection results. Coils composing the electromagnets 4 are fixed to a carrier 6 or support structure. This carrier 6 is engaged with a bowl screw 7 through a bowl (not shown). The bowl screw 7 is attached to a base frame 8 through a shaft retainer 9 and a motor retainer 11. A motor 10 connected to the bowl screw shifts the carrier 6 in a vertical direction. Further, the reaction chamber 2 is provided with fluid conveying means including an upper fluid path 12 and a lower fluid path 13 so as to charge and discharge the reagent and solvent needed for the reactions.

Figure 2:
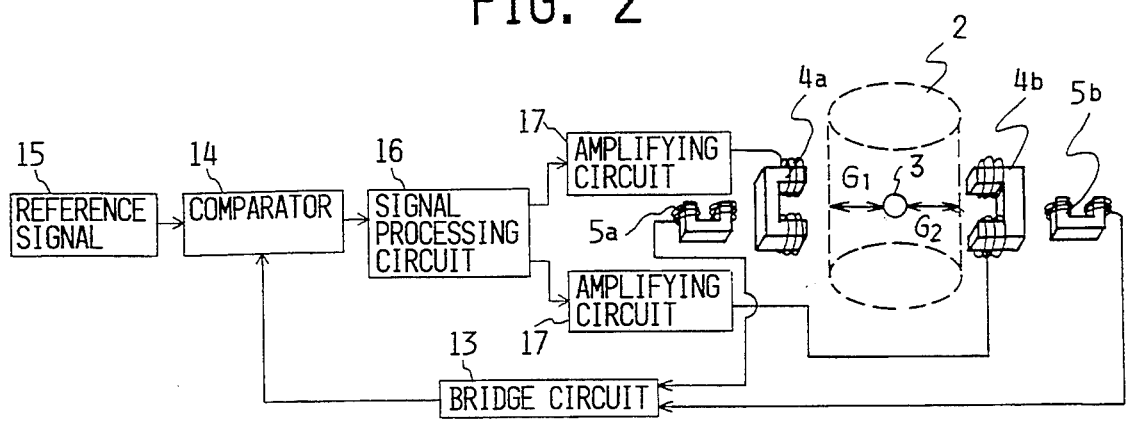

Next, the description is given with reference to FIG. 2 showing the control of the levitating and holding of the sample carrier 3 in the vertical axis by means of the electromagnets 4 and position sensors 5. Firstly, a position sensor 5a detects a distance $G_1$ between an electromagnet 4a and the sample carrier 3 floated by magnetic force generated by the electromagnet 4a and another electromagnet 4b, and another sensor 5b detects a distance $G_2$ between the electromagnet 4b and the sample carrier 3. A bridge circuit 13 processes a pair of detection signals representative of the detected distances $G_1$ and $G_2$, and then a comparator 14 compares the processed signal with a reference signal from a reference signal source 15, and a signal processing circuit 16 calculates appropriate values of electric currents for the electromagnets 4a and 4b based on the compared results. An amplifying circuit 17 amplifies electric currents to the electromagnets according to the calculated values so as to control the magnitude of the magnetic forces generated from the electromagnets 4a and 4b to thereby equalize the distances $G_1$ and $G_2$ with each other and thus prevent the sample carrier 3 from contacting the inner surface of the reaction chamber 2. Further, as described before with reference to FIG. 1, the electromagnet pair 4 is fixed to the movable support 6, and the sample carrier 3 is held by the magnetic attractive forces of the electromagnets 4a and 4b so that the sample carrier 3 can be magnetically displaced and positioned in response to the corresponding displacement of the electromagnet pair 4, i.e., the displacement of the support 6 in parallel manner.

In the above described embodiment, the electromagnet pair 4 and position sensors 5 are aligned in a horizontal direction with respect to the reaction chamber 2 and the sample carrier 3; however, these elements can be aligned in any linear direction such as a vertical direction other than the horizontal direction.

In the inventive reaction vessel, applied reagent and solvent can be efficiently added to the sample on the sample carrier.

Next, the description is given for how to sequentially produce thiazolinon amino acid derivatives from a protein sample carried on the sample carrier and how to detect the derivatives.

Figure 3:
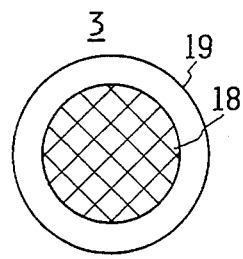
Figure 4:
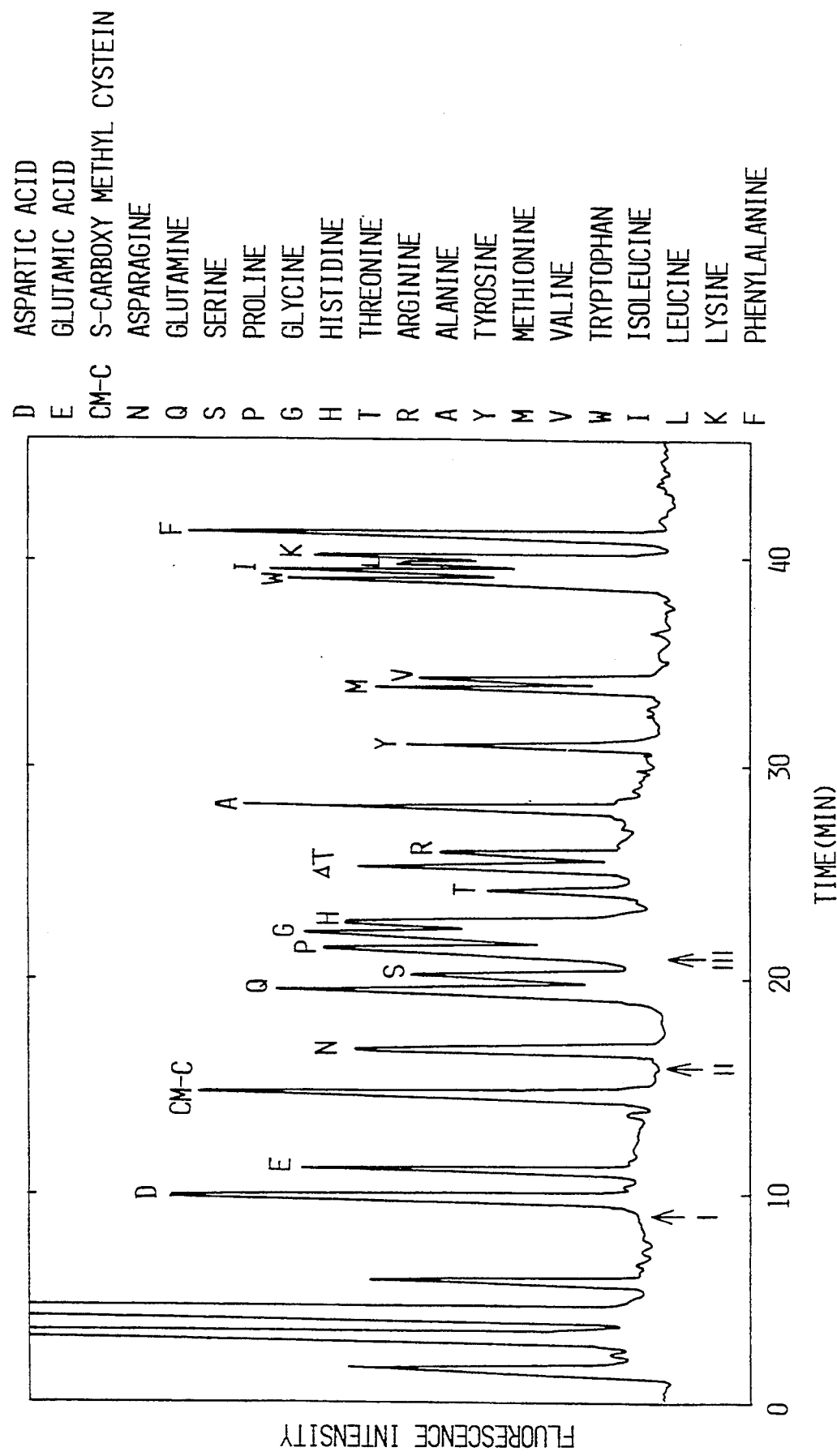

As shown in FIG. 3, the sample carrier 3 is comprised of a ferrite core 18 and a glass coating 19 formed thereon. The coating material can also be selected from ceramic or polymer, including vinylidene fluoride polymer. In such a structure, the ferrite core 18 may have a spheric, cubic, cylindrical or other shape. The following procedure is based on an ordinary automated gas-phase Edman method. The sample carrier 3 having a diameter of 5 mm is treated with polybrene (hexadimethrin bromide) and then is applied with 5 $\mu$l of 70% formic acid containing 1 pico (pico: $10^{-12}$) mole of myoglobin, and thereafter the protein sample is dried. Subsequently, application of a coupling reagent, buffer vapor, washing solvent, cleavage reagent and extraction solvent is delivered to the reaction chamber according to an analysis program (Table 1) of the commercially available automated gas-phase sequence analyzer. Sequentially obtained thiazolinon amino acid derivatives are detected according to fluorescence analysis using 4-amino fluorescein. Namely, 75 $\mu$l of methanol containing 1% of pyridine and 25 $\mu$l of methanol containing 30 pico mole of 4-amino fluorescein are successively added to 150 $\mu$l of butyl chloride containing thiazolinon amino acid derivatives, and the mixture is dried. Next, 25 $\mu$l of methanol containing 30 pico mole of 4-amino fluorescein is added again, and the mixture is dried after 10 minutes of standing. This dried sample is dissolved by 50 $\mu$l of methanol. A 25 $\mu$l portion of the solution is applied to analysis using liquid chromatograph and fluorophotometric detector. Analysis condition is shown in table 2. Further, FIG. 4 shows separation pattern of the standard mixture of 20 kinds of phenylthiocarbamyl amino acid derivatives obtained by the above described procedure. An amount of the respective derivatives is in the order of 10 to 15 femto (femto: $10^{-15}$) mole. All of the derivatives can be identified.

TABLE 1

Cycle Length: 32 steps
Runtime: 43 mins 32 secs

| Step | Function | Value | Elapsed Time |
|---|---|---|---|
| 1 | Prep R2 | 6 | 0 min 6 sec |
| 2 | Deliver R2 | 20 | 0 min 26 sec |

TABLE 1-continued

Cycle Length: 32 steps
Runtime: 43 mins 32 secs

| Step | Function | Value | Elapsed Time |
|---|---|---|---|
| 3 | Prep R1 | 6 | 0 min 32 sec |
| 4 | Deliver R1 | 2 | 0 min 34 sec |
| 5 | Argon Dry | 40 | 1 min 14 sec |
| 6 | Deliver R2 | 400 | 7 min 54 sec |
| 7 | Prep R1 | 6 | 8 min 0 sec |
| 8 | Deliver R1 | 2 | 8 min 2 sec |
| 9 | Argon Dry | 40 | 8 min 42 sec |
| 10 | Deliver R2 | 400 | 15 min 22 sec |
| 11 | Prep R1 | 6 | 15 min 28 sec |
| 12 | Deliver R1 | 2 | 15 min 30 sec |
| 13 | Argon Dry | 40 | 16 min 10 sec |
| 14 | Deliver R2 | 400 | 22 min 50 sec |
| 15 | Argon Dry | 120 | 24 min 50 sec |
| 16 | Deliver S1 | 60 | 25 min 50 sec |
| 17 | Deliver S2 | 200 | 29 min 10 sec |
| 18 | Argon Dry | 120 | 31 min 10 sec |
| 19 | Load R3 | 4 | 31 min 14 sec |
| 20 | Argon Dry | 4 | 31 min 18 sec |
| 21 | Pause | 300 | 36 min 18 sec |
| 22 | Load S2 | 6 | 36 min 24 sec |
| 23 | Block Flush | 6 | 36 min 30 sec |
| 24 | Argon Dry | 120 | 38 min 30 sec |
| 25 | Prep Transfer | 30 | 39 min 0 sec |
| 26 | Deliver S1 | 9 | 39 min 9 sec |
| 27 | Transfer w/S3 | 52 | 40 min 1 sec |
| 28 | Pause | 20 | 40 min 21 sec |
| 29 | Transfer w/Argon | 40 | 41 min 1 sec |
| 30 | End Transfer | 1 | 41 min 2 sec |
| 31 | Deliver S3 | 30 | 41 min 32 sec |
| 32 | Argon Dry | 120 | 43 min 32 sec |

(Extracted from 477 A type manual of Applied Biosystems Co., Ltd.)
R1: 5% phenylisothiocyanate/heptane
R2: 12.5% trimethylamine/water
R3: trifluoroacetic acid
S1: n-heptane
S2: ethyl acetate
S3: butyl chloride

TABLE 2

ANALYSIS CONDITIONS FOR LIQUID CHROMATOGRAPH

Column: Capcell Pack (AG) C18 produced by Shiseido Co., Ltd. $\phi$ 4.5 mm × 150 mm
Column temperature: 43° C.
Detector: spectrofluorophotometer RF-540 produced by Shimazu Seisakusho Co., Ltd.
Excitation wavelength: 494 mm
Emission wavelength: 513 mm
Pump: Waters 600E system
Flow rate: total 0.8 m/min
Gradient program:
(A) 10 mM sodium phosphate buffer
(B) methanol
(C) acetonitrile

| time (min) | (A) % | (B) % | (C) % |
|---|---|---|---|
| 0.0 | 79 | 20 | 1 |
| 0.1 | 75 | 23 | 2 |
| 14.0 | 75 | 23 | 2 |
| 19.0 | 71 | 19 | 12 |
| 34.0 | 71 | 12 | 19 |
| 40.0 | 50 | 25 | 25 |
| 45.0 | 79 | 20 | 1 |
| 65.0 | 79 | 20 | 1 |

Figure 5:
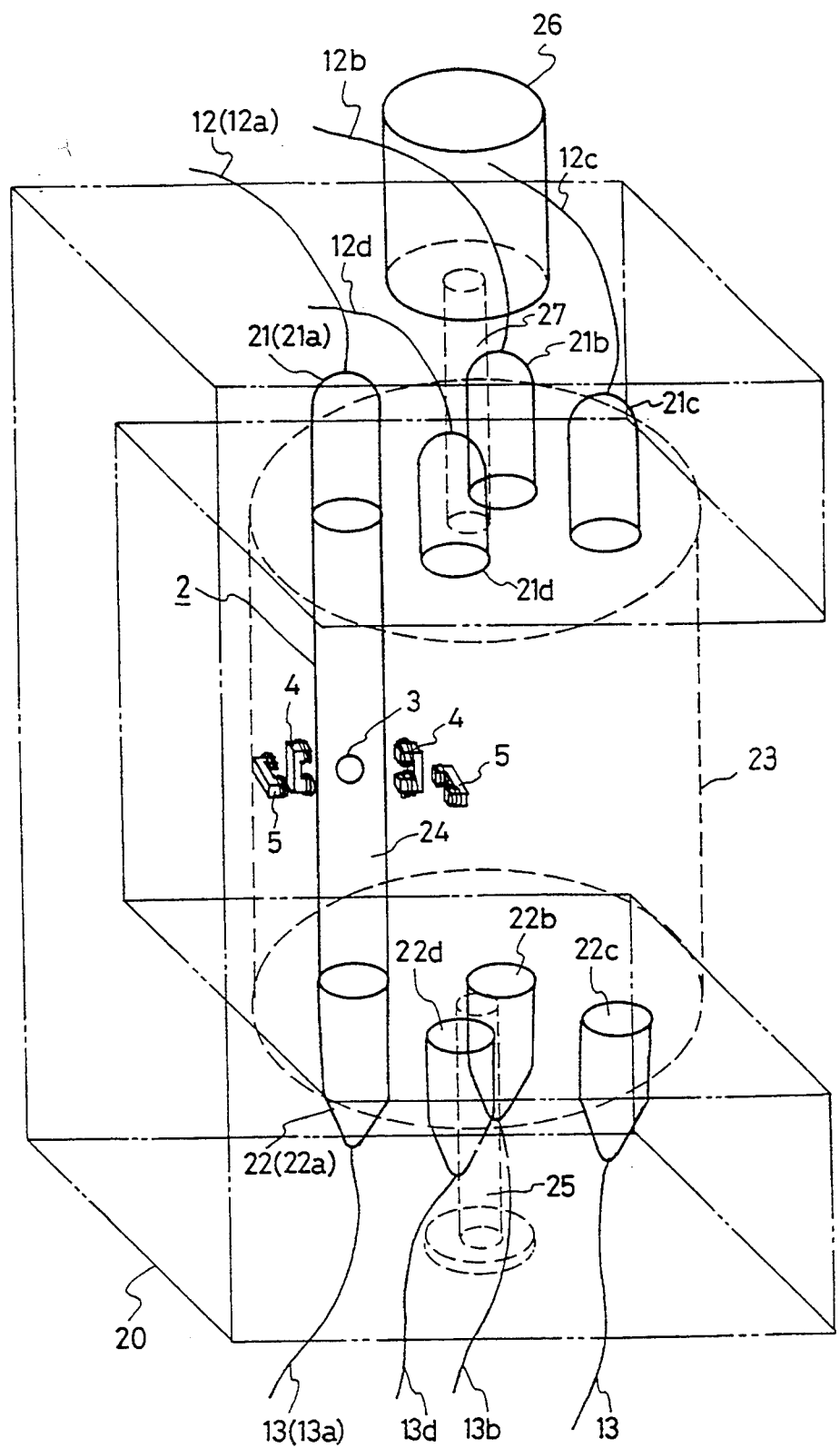
Figure 6:
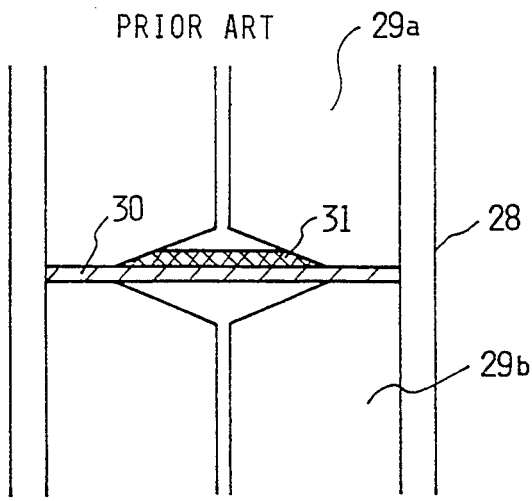
FIGS. 6 and 7 are sectional views of the conventional reaction vessel.
Figure 7:
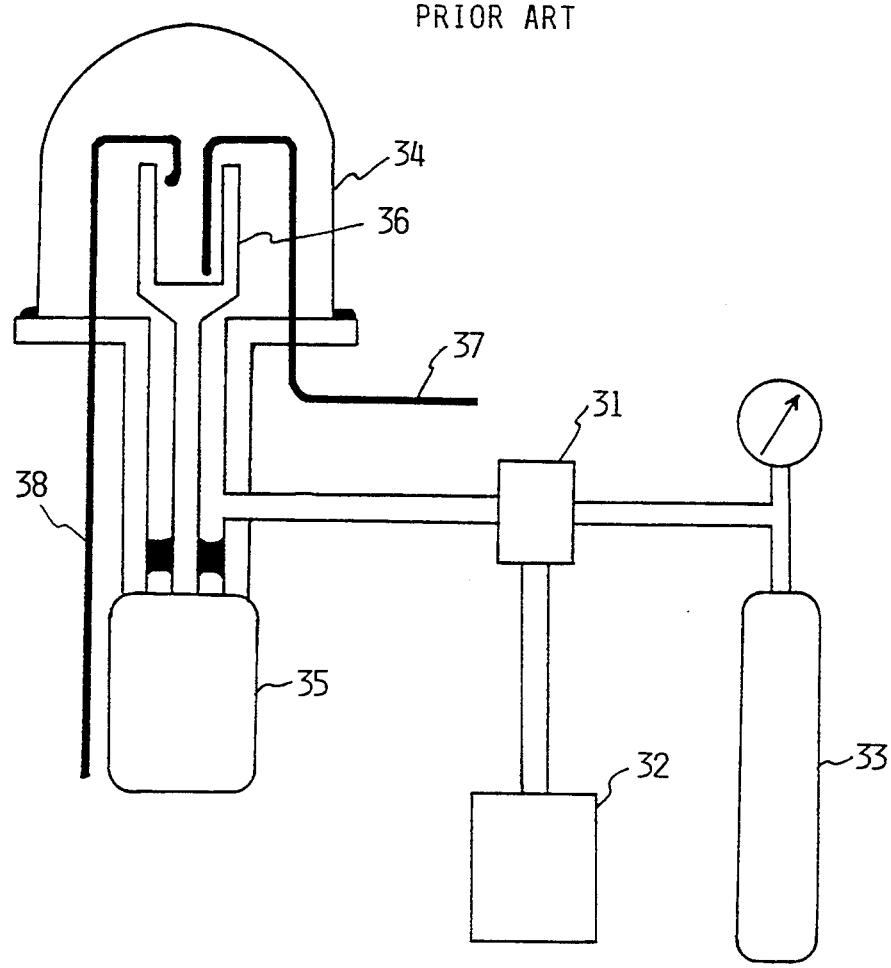

Lastly, the description is given for a second embodiment of the reaction chamber with reference to FIG. 5. The reaction vessel 1 is comprised of a reaction chamber 2 which is constructed by an upper section 21 and a lower section 22 formed in a frame 20 and a central section 24 passed through a rotary drum 23. The rotary drum 23 is supported by a support body 25 and a rotary shaft 27 connected to a motor 26, and is rotationally driven by the motor 26. The upper section 21 has four blind bores 21a, 21b, 21c and 21d, and the lower section 22 has correspondingly four blind bores 22a, 22b, 22c and 24d. Each pair of the corresponding upper and lower bores are aligned in the vertical line with each other and form a separable section, and each pair of the bores can be selectively connected to one another through the central section 24 in the form of a throughhole so as to constitute a closed space defining the reaction chamber 2. The rotary drum 23 is provided with electromagnets 4 and position sensors 5 in opposed relation to the central section 24 so as to float and position a sample carrier 3 in the closed central section 24. Reagents, solvents and inert gases such as argon can be applied through upper fluid paths 12 (12a–12d) and lower fluid paths 13 (13a–13d) to the sample on the carrier 3 in the reaction chamber 2 so as to produce thiazolinon amino acid derivatives. Further, mutual contamination of these reagents and solvents can be avoided as much as possible. In this embodiment, four closed spaces can be provided in the reaction chamber; however, the number thereof can be one, two or more. The arrangement thereof can be linear other than circular as in this embodiment.

As described above, in the reaction vessel or apparatus according to the present invention, the sample carrier is floated and positioned in the reaction chamber, thereby reagents and solvents are efficiently and uniformly effected to the sample, as well as mutual contamination of the used reagents and solvents can be avoided as much as possible.

What is claimed is:

1. A reaction apparatus comprising: means composed of nonmagnetic material defining at least one reaction chamber; fluid conveying means in communication with the reaction chamber for charging reagent and solvent needed for a reaction into the reaction chamber and for discharging reagent and solvent from the reaction chamber; a sample carrier movably disposed in the reaction chamber and comprised of a magnetic material core and a surface coating; magnetic means disposed outside the reaction chamber for generating a magnetic force effective to levitate the sample carrier within the reaction chamber; supporting means for supporting the magnetic means; sensing means for sensing a position of the sample carrier and generating detecting signals; and controlling means operative according to the detecting signals from the sensing means for controlling the magnetic force generated by the magnetic means to thereby adjust the position of the sample carrier.

2. A reaction apparatus according to claim 1; wherein the surface coating is composed of a material selected from a group consisting of glass, ceramics and polymers including vinylidene fluoride polymer.

3. A reaction apparatus according to claim 1; wherein the sample carrier has a smooth surface in the form of a spheric surface or an ellipsoidal surface.

4. A reaction apparatus according to claim 1; wherein the controlling means includes means for preventing the surface of the sample carrier from contacting with an inner face of the reaction chamber.

5. A reaction apparatus according to claim 1; wherein the reaction chamber is comprised of a plurality of separable sections separably connected together to define the reaction chamber.

6. A reaction apparatus according to claim 1; wherein the surface coating of the sample carrier is effective to carry a sample of protein or peptide.

7. A reaction apparatus according to claim 1; including driving means for driving the supporting means vertically with respect to the reaction chamber.

8. A reaction apparatus comprising: means defining a reaction chamber; a sample carrier movable disposed in the reaction chamber; magnetic levitating means for magnetically levitating the sample carrier within the reaction chamber; fluid conveying means in communication with the reaction chamber for charging and discharging reagent and solvent into and from the reaction chamber; supporting means for supporting the magnetic levitating means; and driving means for driving the supporting means relative to the reaction chamber.

9. A reaction apparatus according to claim 8; further comprising sensing means for sensing a position of the sample carrier; and controlling means for controlling the magnetic levitating means dependent on the position sensed by the sensing means.

10. A reaction apparatus according to claim 9; wherein the controlling means includes means for preventing the surface of the sample carrier from contacting with an inner surface of the reaction chamber.

11. A reaction apparatus according to claim 8; wherein the sample carrier has a magnetic material core and a surface coating.

12. A reaction apparatus according to claim 11; wherein the surface coating is composed of a material selected from a group consisting of glass, ceramics, and polymers including vinylidene flouride polymer.

13. A reaction apparatus according to claim 11; wherein the magnetic material core is comprised of ferrite.

14. A reaction apparatus according to claim 11; wherein the surface coating of the sample carrier is effective to carry a sample of protein or peptide.

15. A reaction apparatus according to claim 8; wherein the reaction chamber is comprised of a plurality of separable sections separably connected together to define the reaction chamber.

16. A reaction apparatus according to claim 8; wherein the sample carrier has a smooth surface and is shaped in the form of a sphere or ellipsoid.

* * * * *